United States Patent
Wagner

[11] Patent Number: 6,123,707
[45] Date of Patent: Sep. 26, 2000

[54] REDUCTION INSTRUMENT

[75] Inventor: Erik J. Wagner, Austin, Tex.

[73] Assignee: Spinal Concepts, Inc., Austin, Tex.

[21] Appl. No.: 09/229,297

[22] Filed: Jan. 13, 1999

[51] Int. Cl.[7] .................................................. A61B 17/70
[52] U.S. Cl. .................. 606/61; 606/73; 606/86
[58] Field of Search .................. 606/53, 54, 55, 606/57, 58, 60, 61, 72, 73, 105, 96, 86

[56] References Cited

U.S. PATENT DOCUMENTS

| | | | |
|---|---|---|---|
| 4,505,268 | 3/1985 | Sgandurra | 606/61 |
| 4,611,581 | 9/1986 | Steffee | 606/61 |
| 5,219,349 | 6/1993 | Krag et al. | 606/53 |
| 5,334,205 | 8/1994 | Cain | 606/96 |
| 5,545,166 | 8/1996 | Howland | 606/61 |
| 5,571,102 | 11/1996 | Cavagna et al. | 606/61 |
| 5,630,816 | 5/1997 | Kambin | 606/61 |
| 5,649,926 | 7/1997 | Howland | 606/61 |
| 5,782,831 | 7/1998 | Sherman et al. | 606/61 |
| 5,910,141 | 7/1999 | Morrison et al. | 606/61 |

*Primary Examiner*—Michael Buiz
*Assistant Examiner*—David O. Reip
*Attorney, Agent, or Firm*—Conley, Rose & Tayon, P.C.

[57] ABSTRACT

Devices and instruments for use in spinal alignment or spinal reduction include a connector rod designed to attach to a spinal rod connector, a push rod designed to push against a spinal rod, and a connector member designed to hold the rods in adjustable angular relation. Methods of use are also disclosed.

28 Claims, 4 Drawing Sheets

2

REDUCTION INSTRUMENT

BACKGROUND OF THE INVENTION

1. Field of the Invention

The described invention is in the field of devices and methods of use for correction of spinal deformities or injuries. More particularly, the described devices and methods are directed to a correction of spondylolisthesis by spinal reduction, or repositioning of the spine to a more normal configuration.

2. Description of Related Art

Spondylolisthesis is a forward movement or slippage of a lower lumbar vertebra on the vertebra below it, or on the sacrum. When a spinal fusion is necessary or recommended, a physician must decide whether to do a reduction, or to fuse the vertebra in the forward position. The latter is often done because of the danger of nerve or tissue damage associated with reduction. Early methods of spinal reduction included cable systems that were attached to a vertebra and connected to an external system of traction weights.

An apparatus for spinal reduction is described in U.S. Pat. No. 4,611,581 to Steffee. The apparatus includes a spinal plate or a pair of plates that may be screwed to several adjacent vertebrae. A bone screw in the displaced vertebra is attached to, or includes a threaded rod, which then passes through an opening in the plate. By means of tightening a nut on the threaded rod, the misalignment may be reduced.

Another system is described in U.S. Pat. No. 5,782,831, to Sherman et al. In the described system, a cable is attached, either directly or indirectly to a bone screw in a misaligned vertebra. The cable may then be attached to an anchor on a spinal rod running along the spinal column. A cable tensioning device is then used to apply tension to the displaced vertebra to pull it into the desired position.

Because of the natural curvature of the spine, and the shape of individual vertebrae, a misaligned vertebra typically needs to be pulled in a direction that is not parallel to the long axis of a bone screw in that vertebra. It is, in fact, the need to apply a non-parallel force that may be a cause of damage to nerve or soft tissue, or even failure of the bone. There is a need therefore, for a system for spinal reduction in which a force can be applied to a misaligned vertebra in the desired direction when that direction is not parallel to the long axis of a bone screw in that vertebra.

SUMMARY OF THE INVENTION

Described herein are devices for spinal reduction. Such devices, in certain embodiments, may include two elongated members and a connecting member that maintains the two elongated members in adjustable angular relation to each other during use. In certain embodiments, a first elongated member or a connector rod may include an attachment end configured to attach to a spinal rod connector or a fixation device during use. When the device is configured to be operated in conjunction with a spinal rod assembly, the attachment end of the first elongated member may be configured to attach to a spinal rod connector that is attachable to a fixation device. In certain embodiments the first elongated member is a hollow tube or barrel forming an interior channel. An inner shaft or rod may be disposed in the interior channel during use. The inner shaft may extend above the outer barrel so that an operator of the device may grip the inner shaft and turn it to threadably advance the inner shaft through the barrel, or to slide the inner shaft through the barrel during use. The first elongated member may also be a solid rod or shaft in certain embodiments, with an attachment end that is configured to grip a spinal rod connector.

The spinal rod connector may be any connector known in the art, and particularly preferred are connectors configured to connect a spinal fixation device to a spinal rod. Such devices would include a screw such as a bone screw or pedicle screw, a hook or a transverse connector, for example, and would include connectors disclosed in U.S. patent application Ser. Nos. 08/740,123, 08/942,325, 09/026,711, 09/059,162, 09/070,234 and 09/070,268, each incorporated by reference, in their entirety, herein.

In certain embodiments of the described devices, the attachment end of the first elongated member is movable from a locked configuration to an unlocked configuration. For example, the first elongated member may include a threaded inner shaft disposed in an outer barrel with mating internal threads. In such an arrangement, turning the inner shaft with respect to the outer shaft may be effective to reversibly move the attachment end from a locked configuration to an unlocked configuration. In such a configuration, threadably advancing the inner shaft through the outer barrel may move an end of the inner shaft out of an opening in the outer barrel at the attachment end so that the inner shaft may contact and press against a connector when present. In certain embodiments the attachment end of the first elongated member includes a horizontal channel defined by two opposing arms ending in inward facing flanges that are configured to slide in grooves on the sides of a spinal rod connector. By "horizontal" it is meant that the channel is substantially perpendicular to the long axis of the elongated member. When the flanges are in the grooves during use, the connector rod is constrained from moving vertically. Causing the inner shaft to press against a connector in the channel, by turning the shaft, for example, locks the elongated member to the connector.

In alternative embodiments, the attachment end of the first elongated member may include a pair of moveable projections or arms that move from an open configuration to a closed configuration by moving an inner shaft with respect to an outer barrel. In such devices, the inner shaft may either slide in the barrel, or it may include threads as in the previously described embodiment. Moving the inner shaft up or down with respect to the barrel may cause the arms to close and grip a spinal rod connector, thus causing them to assume the locked configuration.

Devices described herein may include a second elongated member or a push rod, one end of which may be configured to engage a spinal rod during use. In certain embodiments, the end that engages a spinal rod may include a pusher end that is attached to the second elongated member and may be freely rotatable with respect to the second elongated member. The pusher end may include a void or opening configured to contact or at least partially surround a spinal rod. In certain embodiments, the void is of the same shape as a spinal rod and conforms to the exterior of a spinal rod during use. For example, if a spinal rod is round, the void in the pusher end may include a semicircular shape of the same diameter as the spinal rod.

Devices described herein may also include a connecting member or a plate configured to engage the second elongated member with an adjustable engagement point. The engagement point may be adjustable along at least a part of the length of the second elongated member, so that the push rod may be moved up or down with respect to the connecting member to press against a spinal rod during use. A device may further include a locking mechanism configured to secure the connecting member to the first elongated member. In certain embodiments the connecting member may include an opening or a threaded opening configured to hold the second elongated member. In those embodiments in which the opening is threaded, the second elongated member may include a threaded region on the exterior thereof that is configured to mate with the threads in the threaded opening. In those embodiments, the second elongated member may be threaded through the connecting member to contact and press against a spinal rod during use.

The connecting member may also include an arcuate track configured to provide a slidable adjustment of the angle between a rod secured to one end of the connecting member and a rod moveable along, or in the track. A locking mechanism may also be provided to stop the first elongated member against the connecting member. In certain embodiments the locking mechanism may include an eyebolt, including an eye portion connected to a projection, preferably a threaded projection. In certain embodiments the eyebolt may be configured so the first elongated member may slide through the eye of the eyebolt, and the bolt or threaded projection may extend through a track in the connecting member. A nut or knob may then be provided to mate with the threaded member of the eyebolt. When an elongated member of the device is held in the eyebolt during use, the eyebolt may slide in a track in the connecting member until the desired angle between a first and second elongated member is achieved. When the desired angle is achieved, a nut or knob may be tightened on the threaded projection extending through the track, drawing the elongated member to press against the connecting member, and locking the elongated member or connector rod in place.

Disclosed herein are also methods of aligning a vertebra in a subject including providing a first elongated member comprising an attachment end configured to attach to a spinal rod connector during use; providing a second elongated member, wherein one end thereof is configured to contact a spinal rod during use; providing a connecting member configured to engage the second elongated member, wherein the engagement point is adjustable along at least a part of the length of the second elongated member, and wherein the connecting member is configured to provide an adjustable angle between the first elongated member and the second elongated member during use; providing a locking mechanism configured to secure the connecting member to the first elongated member; providing an anchored spinal rod in the region of the vertebra; engaging a spinal rod connector with the attachment end of the first elongated member; contacting the anchored spinal rod with the second elongated member; adjusting the angle between the first and second elongated members such that the second elongated member is oriented in the direction of alignment; activating the locking mechanism effective to lock the first elongated member with respect to the connecting member; and adjusting the engagement point of the second elongated member and the connecting member effective to push the second elongated member against the spinal rod until the desired alignment is attained. When the desired alignment is reached, one may connect the spinal rod connector to the spinal rod to hold the realigned vertebra in place. It is understood that a spinal realignment typically involves duplicating the method with at least one device on each side of a spine.

Described herein are also methods of altering the alignment of a misaligned vertebra, wherein the misaligned vertebra contains a bone screw, and wherein the method includes providing a rod connected to the vertebra; providing a second rod in contact with a spinal rod anchored to a vertebra near the misaligned vertebra; providing a connector attached to the two rods; orienting the first rod in the direction of a bone screw in the misaligned vertebra; orienting the second rod in the direction of the altered alignment; and causing the second rod to press against the spinal rod effective to move the vertebra with respect to the spinal rod until the altered alignment is achieved. One may also connect the bone screw connector to the spinal rod after alignment is complete. This method is also preferably duplicated on the two sides of a spine.

A method of manufacturing a spinal reduction device is an embodiment of the present disclosure. These methods include providing a first elongated member comprising an attachment end configured to attach to a spinal rod connector during use; providing a second elongated member, wherein one end thereof is configured to contact a spinal rod during use; providing a connecting member configured to engage the second elongated member, wherein the engagement point is adjustable along at least a part of the length of the second elongated member, and wherein the connecting member is configured to provide an adjustable angle between the first elongated member and the second elongated member during use; and providing a locking mechanism configured to secure the connecting member to the first elongated member during use.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
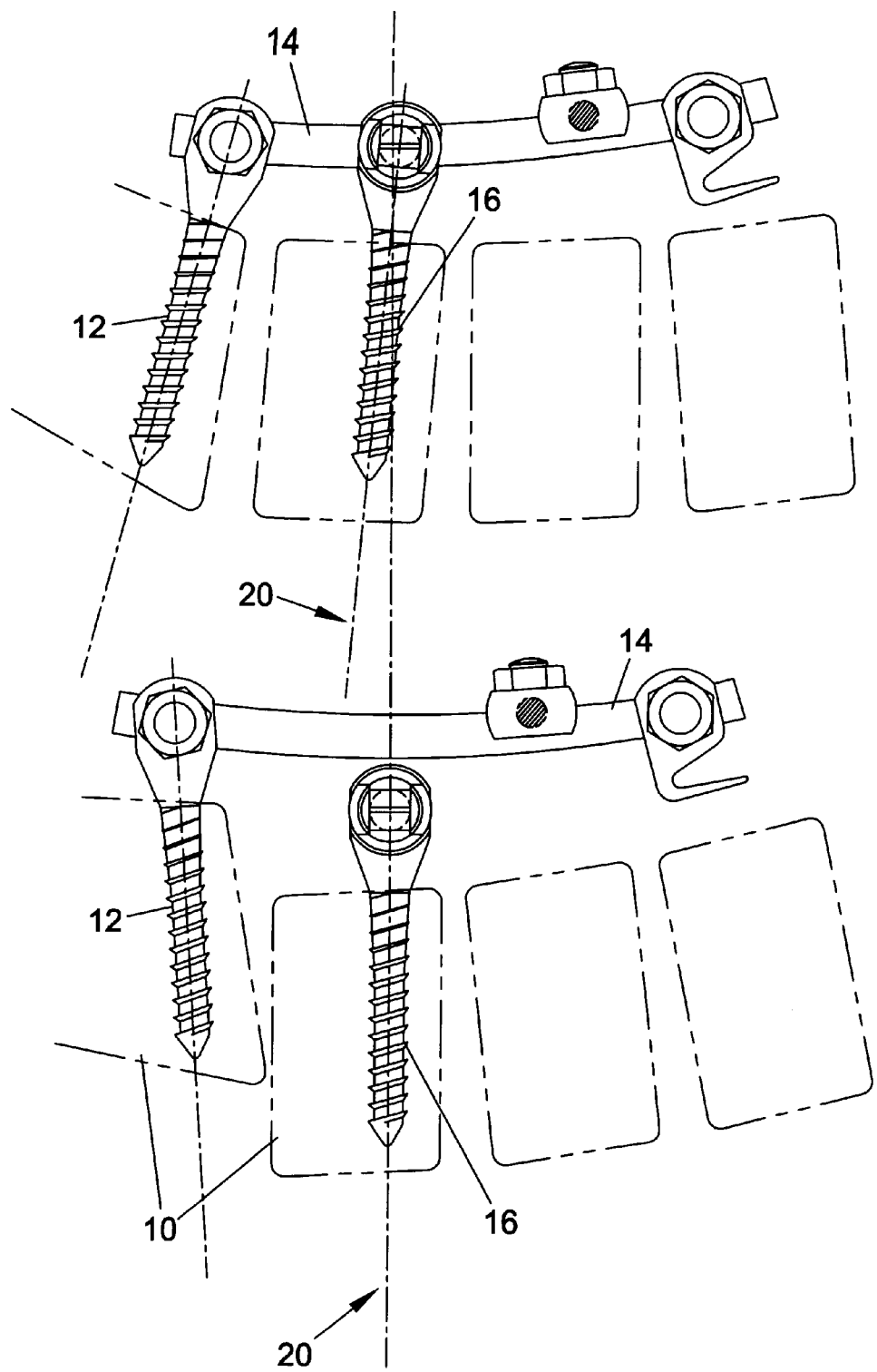
FIG. 1 demonstrates correction of a spinal misalignment in a direction that is not parallel to the long axis of a bone screw in that vertebra.

FIG. 1 demonstrates the principle of pulling a spine into alignment along a direction that is not parallel to a bone screw in the misaligned vertebra. In the drawing, a portion of a spinal column is depicted with the vertebrae 10 misaligned in the lower section and correctly aligned in the upper section of the drawing. Bone screws 12 and 16 are shown in place in two of the vertebrae. Also shown is a spinal rod 14 that is anchored to one of the bone screws. The long axis of a bone screw 16 is shown as the line at 20. Also shown in the drawing is the long axis of the bone screw 14. As described herein, spinal distraction involves moving the vertebrae back into correct alignment as shown in the upper section of the drawing. The disclosed device may be connected to bone screw 16 such that the connector rod is aligned with the long axis of screw 16, and the push rod would be angled in the direction of motion of the vertebra. As the head of the bone screw reaches the rod 14, the vertebrae are in correct alignment. The direction of movement of the vertebra can be seen by comparison of the long axis of bone screw 16 in the aligned and misaligned spine. As can also be seen from the drawing, the angle between the bone screw 12 and the rod 14 has also changed as the spine is pulled back into a more correct alignment.

Figures 2A, 2B:
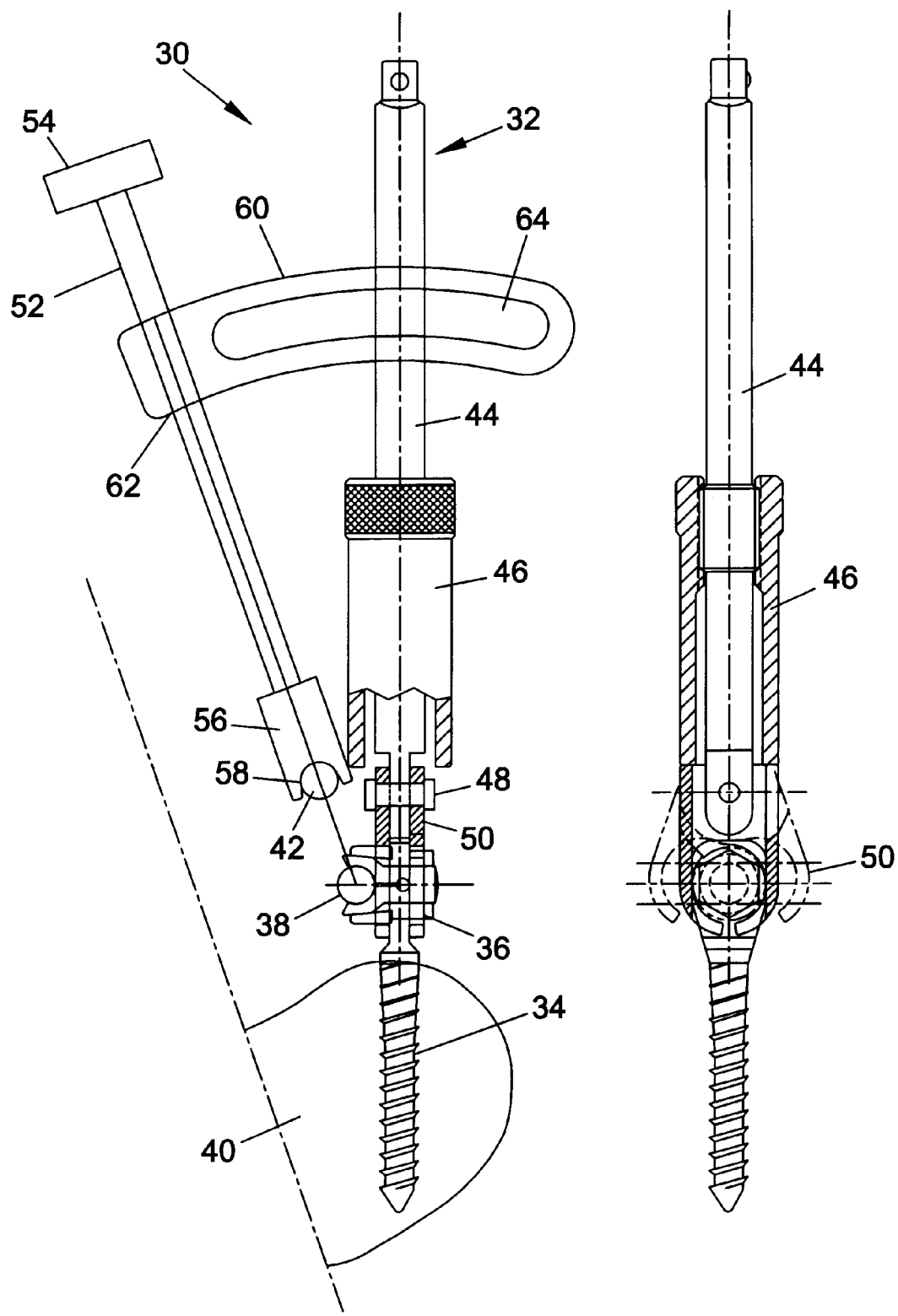
FIG. 2A is a schematic front view of an embodiment of a spinal reduction device.
FIG. 2B is a schematic side view of the device shown in FIG. 2A.

FIGS. 2A and 2B demonstrate an embodiment of a reduction device 30 in use. The device includes an elongated member, or connector rod 32 that connects to a bone screw 34, screwed into a vertebra 40, either directly or indirectly through a spinal rod connector 36. The connector 36 is shown as providing a channel 38 to accept a spinal rod 42. The elongated member 32 may include a shaft 44 and a barrel or hollow tube 46 threaded onto the shaft 44. In the embodiment shown, the shaft is connected by a pin 48 to a set of arms 50. As shown in FIG. 2B, as the shaft 44 is moved upward relative to the barrel 46, by threadable advancement, the arms 50 are caused to grip the spinal rod connector 36.

The device 30 also includes another elongated member or rod 52. Rod 52 may also be described as a push rod. The rod 52 may include a knob 54 and a pusher end 56. The pusher end 56 may provide a groove 58 or void configured to hold a spinal rod 42. A plate 60 connects member 52 to member 32. The plate 60 provides a threaded opening 62 that accommodates the shaft 52. Shaft 52 is threaded so that turning the shaft 52 advances the shaft 52 with respect to the plate 60. Shaft 44 is preferably connected to the plate 60 by a connector (not shown) that is slidable in the channel 64. A preferred connector is an eyebolt that connects to the shaft 44, passes through the channel 64, and provides a threaded projection for a nut. When the nut is tightened, shaft 44 is locked in position in the channel 64.

Figure 3A:
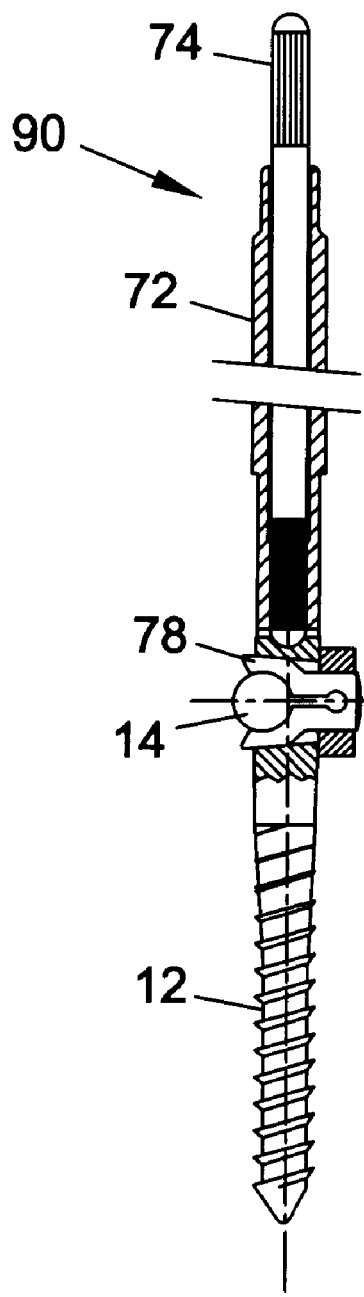
FIG. 3A is a schematic side view of an embodiment of a spinal reduction device.
Figure 3B:
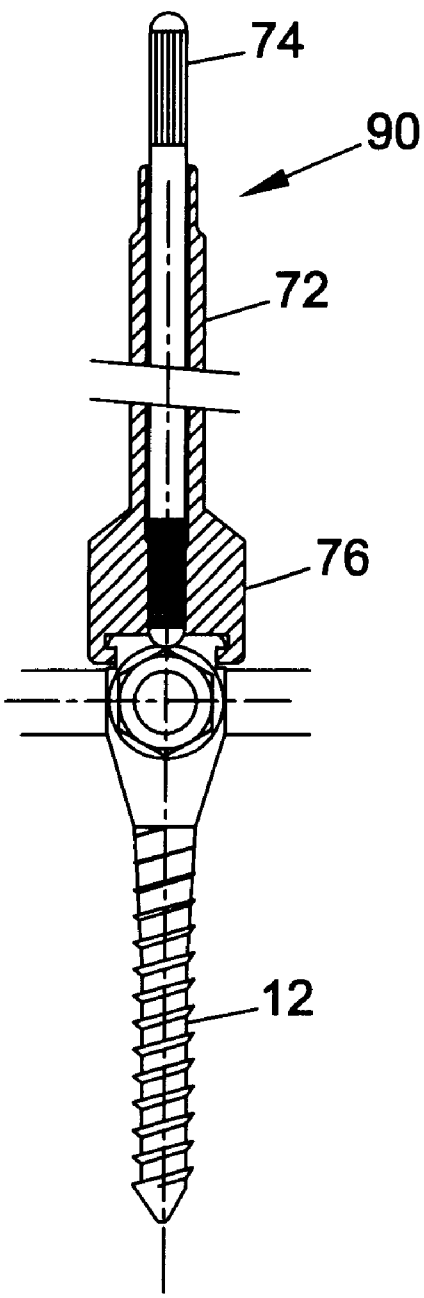
FIG. 3B is a schematic front view of an embodiment of a spinal reduction device.

An alternate embodiment of a device is shown in FIG. 3A. In this embodiment, the connector rod 90 includes a threaded shaft 74 disposed inside an outer barrel 72 with mating threads. The barrel includes a connector 76 that is configured to clip onto a bone screw/spinal rod connector 78. Threadably advancing the inner shaft 74 through the barrel 72 causes the inner shaft 74 to contact a spinal rod connector 78 clipped to the connector 76, thus firmly holding the shaft 74 to the spinal rod connector 78.

Figure 4:
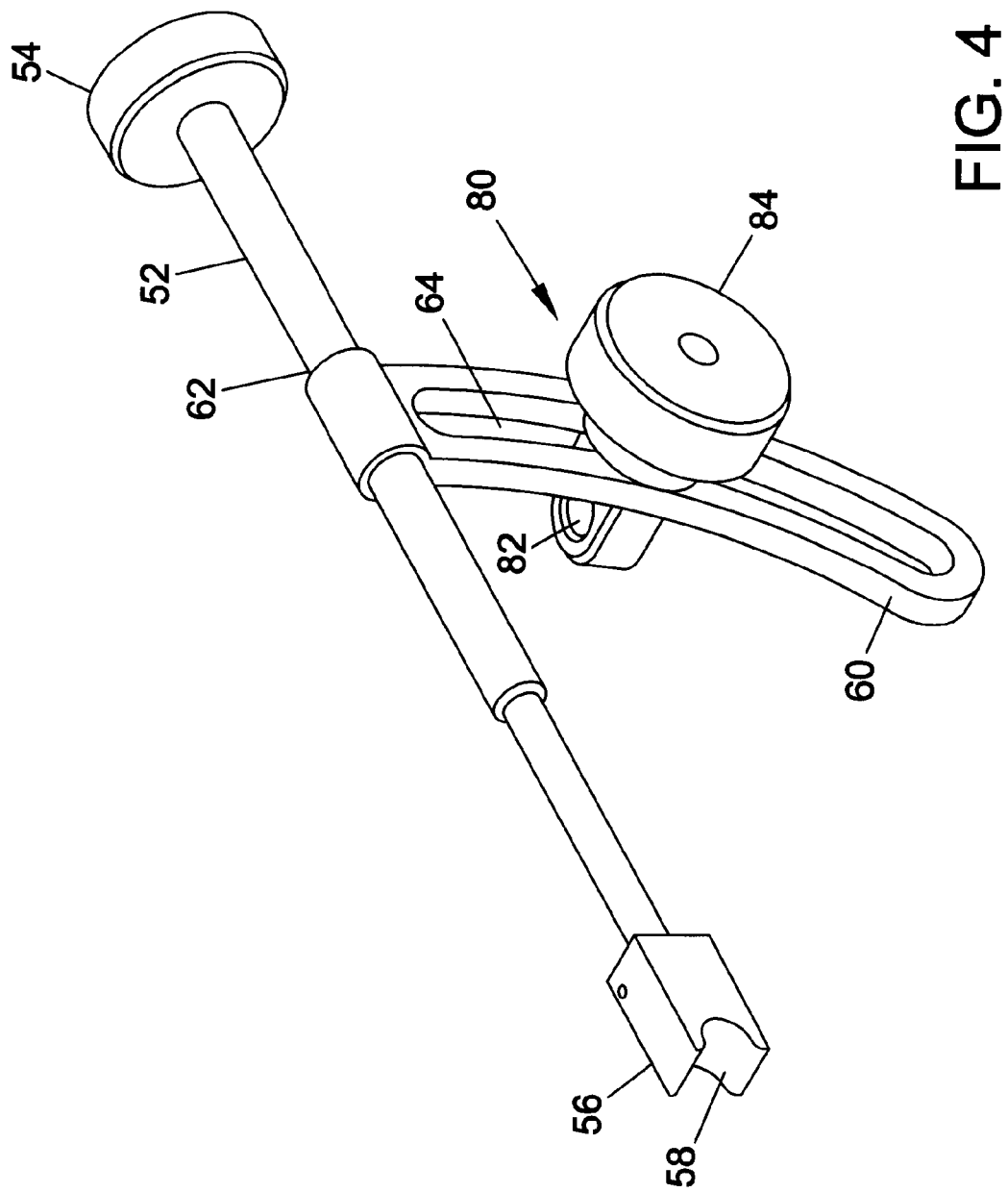
FIG. 4 is a perspective view of an embodiment of a spinal reduction device.

FIG. 4 shows an embodiment of the described device in which an eyebolt is disposed in channel 64. The eyebolt provides an opening 82 to hold a connector rod. As shown, knob 84 may be threaded onto the eyebolt and tightened against the plate 60 to hold the rod in place.

During use of a device described herein, a physician places a spinal rod, or preferably a spinal rod on each side of a spine, and anchors the spinal rod with spinal hooks, pedicle screws, or other means attached to vertebrae of the spine. The rod may also be anchored to at least one vertebrae near the vertebra to be repositioned. The misaligned vertebra may be tapped and a bone screw or pedicle screw may be threaded into the vertebra, and a connector configured to connect the bone screw to a spinal rod may be attached to the screw. It is understood that all the steps described in this paragraph are done in preparation for use of a reduction device as described herein, and that any method that results in an anchored spinal rod and a misaligned vertebra with a bone connecting device in place may be used.

The device may be assembled by placing a connector rod 90 in the opening 82 in eyebolt 80, extending the bolt through the track 64 in the plate 60, and loosely threading the knob 84 on the bolt. The knob may be tightened only enough to allow easy handling of the device. The connector 90 may be attached to a spinal rod connector 78 and tightened by turning the inner shaft 74. In the embodiment shown in FIGS. 2A and 2B, the shaft 32 is turned, causing arms 50 to grasp the connector 36.

The push rod may be disposed in the opening 62 in the plate 60 and threadably advanced through the opening until the pusher end 56 contacts the spinal rod 42. The knob 84 may then be loosened so that the angle between the connector rod 90 and the push rod 52 can be adjusted by sliding the eyebolt 80 in the channel 64. The adjustment may be made until the push rod 52 is positioned along the direction, or in the axis of the desired movement of the vertebra. In other words, the movement of the vertebra will be along a line defined by the push rod. This method reduces the stress on the bone and reduces the chance of damage to the nerves and soft tissues. When the push rod 52 is properly aligned, knob 84 may be tightened to lock the angle between the rods. Then push rod 52 may be turned, preferably using the knob 54 to pull the vertebra in the desired direction. When reduction is complete, the bone screw that is held by the connector rod may be connected to the spinal rod. In the practice of the invention, it is understood that two or more of the devices described may be used simultaneously, one or more on either side of the vertebra so that the realignment may be more easily and precisely controlled.

While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A device for spinal reduction comprising:
   a first elongated member, comprising an attachment end configured to attach to a spinal rod connector during use;
   a second elongated member, wherein one end thereof is configured to contact a spinal rod during use;
   a connecting member configured to engage the second elongated member, wherein the engagement point is adjustable along at least a part of the length of the second elongated member; and
   a locking mechanism configured to secure the connecting member to the first elongated member;
   wherein the connecting member is configured to provide an adjustable angle between the first elongated member and the second elongated member during use.

2. The device of claim 1, wherein the attachment end of the first elongated member is movable from a locked configuration to an unlocked configuration.

3. The device of claim 2 wherein the first elongated member comprises a threaded inner shaft disposed in an outer shaft with mating internal threads, and wherein turning the inner shaft with respect to the outer shaft is effective to reversibly move the attachment end from a locked configuration to an unlocked configuration.

4. The device of claim 3, wherein the attachment end comprises a channel configured to receive a spinal rod connector.

5. The device of claim 4, wherein turning the inner shaft threadably advances an end of the inner shaft into the channel and wherein the end of the inner shaft presses against a spinal rod connector in the channel during use.

6. The device of claim 2, wherein the attachment end comprises a pair of moveable projections that grip a spinal rod connector in the locked configuration.

7. The device of claim 1, wherein the end of the second elongated member that is configured to contact a spinal rod is freely rotatable with respect to the elongated member.

8. The device of claim 7, wherein the freely rotatable end comprises a void configured to receive a spinal rod.

9. The device of claim 1, wherein the second elongated member comprises a threaded region.

10. The device of claim 9, wherein the connecting member comprises a threaded opening configured to threadably mate with the threaded region of the second elongated member.

11. The device of claim 1, wherein the connecting member comprises an arcuate channel.

12. The device of claim 11, wherein the locking mechanism comprises an eyebolt, wherein the eye of the eyebolt is configured to hold the first elongated member and wherein the eyebolt is slidable in the arcuate channel.

13. A spinal reduction instrument, comprising:
   an elongated push rod;
   a connector rod comprising a member configured to connect to a fixation device; and
   a plate;
wherein the plate is configured to provide a connection between the push rod and the connector rod so that the push rod and the connector rod are held in adjustable angular relation, and further wherein the push rod is moveable along at least a portion of its length with respect to the plate.

14. The instrument of claim 13, wherein the instrument comprises an eyebolt configured to hold the connector rod in the eye of the eyebolt and to provide a threaded projection through the plate, so that turning a threaded member on the threaded projection is effective to press the connector rod against the plate.

15. The instrument of claim 14, wherein the plate provides an arcuate channel configured such that the eyebolt is slidable in the channel.

16. The instrument of claim 14, wherein the threaded member is a knob.

17. A device for spinal reduction comprising:
   a first elongated member, comprising an attachment end configured to attach to a spinal rod connector during use, wherein the first elongated member comprises a threaded inner shaft disposed in an outer shaft with mating internal threads, and wherein turning the inner shaft with respect to the outer shaft is effective to reversibly move the attachment end from a locked configuration to an unlocked configuration;
   a second elongated member, wherein at least a part of the second elongated member comprises threading, and wherein one end thereof is configured to contact a spinal rod during use;
   a connecting member comprising a threaded opening configured such that the second elongated member is threadable through the threaded opening; and
   a locking mechanism configured to secure the connecting member to the first elongated member;
   wherein the connecting member is configured to provide an adjustable angle between the first elongated member and the second elongated member during use.

18. The device of claim 17, wherein the attachment end comprises a channel configured to receive a spinal rod connector, and wherein turning the inner shaft threadably advances an end of the inner shaft into the channel effective to press the inner shaft against a spinal rod connector in the channel during use.

19. The device of claim 17, wherein the attachment end comprises a pair of moveable projections configured to reversibly grip a spinal rod connector during use.

20. The device of claim 17, wherein the end of the second elongated member that is configured to contact a spinal rod is freely rotatable with respect to the elongated member.

21. The device of claim 17, wherein the end of the second elongated member that is configured to contact a spinal rod comprises a void configured to receive a spinal rod.

22. The device of claim 21, wherein the void is semicircular.

23. The device of claim 17, wherein the connecting member comprises an arcuate channel.

24. The device of claim 23, wherein the locking member comprises an eyebolt, wherein the eye of the eyebolt is configured to hold the first elongated member and wherein the eyebolt is slidable in the arcuate channel.

25. A method of manufacturing a spinal reduction device comprising:
   providing a first elongated member comprising an attachment end configured to attach to a spinal rod connector during use;
   providing a second elongated member, wherein one end thereof is configured to contact a spinal rod during use;
   providing a connecting member configured to engage the second elongated member, wherein the engagement point is adjustable along at least a part of the length of the second elongated member, and wherein the connecting member is configured to provide an adjustable angle between the first elongated member and the second elongated member during use; and
   providing a locking mechanism configured to secure the connecting member to the first elongated member during use.

26. A spinal reduction instrument, comprising:
   an elongated push rod;
   a connector rod; and
   a plate;
   an eyebolt configured to hold the connector rod in the eye of the eyebolt and to provide a threaded projection through the plate, so that turning a threaded member on the threaded projection is effective to press the connector rod against the plate;
   wherein the plate is configured to provide a connection between the push rod and the connector rod so that the push rod and the connector rod are held in adjustable angular relation, and further wherein the push rod is moveable along at least a portion of its length with respect to the plate.

27. The instrument of claim 26, wherein the plate provides an arcuate channel configured such that the eyebolt is slidable in the channel.

28. The instrument of claim 26, wherein the threaded member is a knob.

* * * * *